(12) United States Patent
St. George

(10) Patent No.: US 6,177,581 B1
(45) Date of Patent: Jan. 23, 2001

(54) MIXED-METAL CHELATES AND PROCESS FOR THE PREPARATION THEREOF

(75) Inventor: George M. St. George, Jones Creek, TX (US)

(73) Assignee: The Dow Chemical Company, Midland, MI (US)

(*) Notice: Under 35 U.S.C. 154(b), the term of this patent shall be extended for 0 days.

(21) Appl. No.: 09/415,962

(22) Filed: Oct. 12, 1999

(51) Int. Cl.⁷ .............................. C07F 15/02; C07F 15/06; C07F 11/00
(52) U.S. Cl. .............................. 556/62; 556/63; 556/148; 534/16
(58) Field of Search .............................. 556/62, 63, 148; 534/16

(56) References Cited

U.S. PATENT DOCUMENTS

| | | | |
|---|---|---|---|
| 5,159,094 | * 10/1992 | Thunberg | 556/148 |
| 5,274,151 | * 12/1993 | Thunberg | 556/148 |
| 5,446,179 | * 8/1995 | Thunberg | 556/148 |
| 5,962,717 | * 10/1999 | Nonomura et al. | 556/50 |

OTHER PUBLICATIONS

Schugar et al., Journal of the American Chemical Society, vol. 89, No. 15, 3712, 1967.*

* cited by examiner

Primary Examiner—Porfirio Nazario-Gonzalez

(57) ABSTRACT

Mixed-metal chelates represented by the following general formula

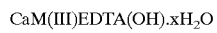

$CaM(III)EDTA(OH) \cdot xH_2O$ wherein M is a trivalent transition metal and x is 0, 0.5, 1, 1.5, 2, 2.5, 3, 3.5, 4, 4.5, 5, 5.5, 6, 6.5, 7, 7.5, or 8 and a process for their preparation are disclosed. The process comprises the steps of a) reacting calcium hydroxide or calcium oxide, ethylenediaminetetraacetic acid, and a transition metal-containing material in an aqueous medium, optionally in the presence of an oxidant to convert any transition metal present in a divalent form to its trivalent form; and b) separating the formed mixed-metal chelate by filtration or evaporation. These mixed-metal chelates are useful as catalyst precursors and dietary supplements.

24 Claims, No Drawings

MIXED-METAL CHELATES AND PROCESS FOR THE PREPARATION THEREOF

The present invention relates to mixed-metal chelates and a process for the preparation thereof.

BACKGROUND OF THE INVENTION

Compositions containing two or more different metals have found use in several areas. Sometimes the compositions themselves can act as catalysts; more often, they behave as catalyst precursors, being transformed into active catalysts by reduction to give alloys or thin films or by oxidation (calcination) to give mixed-metal oxides. These oxides may behave as ceramics as well as catalysts. Often, these mixed-metal compositions are simple mixtures of single-metal compounds. Reduction or calcination of such mixtures can give non-homogeneous products because of incomplete mixing of the compounds, resulting in monometallic domains. When possible, it is advantageous to use as precursors unique compounds containing the desired metal ratio, because the metals will be intimately mixed, even at the molecular level.

Mixtures of metals have other uses, as well. For example, iron, zinc, and magnesium are found in agricultural nutrient formulations, whereas iron, zinc, chromium, cobalt, and calcium are found in animal and human dietary supplements. Routinely, these sorts of formulations contain mixtures of compounds, each compound containing one of the desired metals. To reduce the amount of ancillary organic material in these formulations, it can be advantageous to provide two or more metals in a single compound, thereby increasing the percentage of metals vis-à-vis the organic ligands.

Iron chelates are a class of compounds that have found use in natural gas treating, photographic bleaching, fertilizers, and dietary supplements. Routinely, said iron chelates are used as ammonium or alkali metal salts. In such cases, the alkali metal or ammonium ion provides charge balance but otherwise imparts no useful properties to the iron chelate. For example, sodium ferric ethylenediaminetetraacetate (NaFeEDTA) has been used for iron fortification in foods. The iron provided is beneficial, but the sodium is possibly hazardous to those people requiring a low-sodium diet. On the other hand, iron chelate complexes with calcium can potentially be used to provide the dietary benefits of both metals.

Because of its tetravalent nature, ethylenediaminetetraacetic acid (EDTA) can conceivably combine with a divalent and a trivalent metal to form complexes of the general formula $M(II)M'(III)EDTA(OH).xH_2O$. To our knowledge no such mixed-metal complexes of EDTA have been reported in the literature.

The calcium salt of the ferric chelate of a similar ligand, hydroxyethylethylenediaminetriacetate (HEDTA), was reported as an amorphous, red solid (without analytical data) by Schugar, et al. in J. Amer. Chem. Soc., 89, 3712 (1967).

There is clearly a need for transition metal chelate, particularly iron chelate, complexes with calcium which can be used to provide the dietary benefits of both metals.

The present invention offers such transition metal chelate complexes with calcium and a process for their preparation.

SUMMARY OF THE INVENTION

In one aspect the present invention relates to mixed-metal chelates represented by the following general formula $$CaM(III)EDTA(OH).xH_2O$$

wherein M is a trivalent transition metal and x is 0, 0.5, 1, 1.5, 2, 2.5, 3, 3.5, 4, 4.5, 5, 5.5, 6, 6.5, 7, 7.5, or 8.

In another aspect the present invention relates to a process for preparing mixed-metal chelates of the general formula $CaM(III)EDTA(OH).xH_2O$, wherein M is a transition metal and x is 0, 0.5, 1, 1.5, 2, 2.5, 3, 3.5, 4, 4.5, 5, 5.5, 6, 6.5, 7, 7.5, or 8, said process comprising the steps of a) reacting calcium hydroxide or calcium oxide, ethylenediaminetetraacetic acid, and a transition metal-containing material in an aqueous medium, optionally in the presence of an oxidant to convert any transition metal present in a divalent form to its trivalent form; and b) separating the formed mixed-metal chelate by filtration or evaporation.

DETAILED DESCRIPTION OF THE INVENTION

In the context of the present invention, the general formula $CaM(III)EDTA(OH).xH_2O$ is an empirical formula and is intended to include structures of higher nuclearity, such as, for example, $Ca_2[M(III)_2(EDTA)_2O].xH_2O$. The amount of water of hydration, "x", is dependent both on M and the conditions of preparation.

For the purposes of this invention, the term transition metal includes the metals of the lanthanide series. The transition metal contemplated by the foregoing general formula may be any transition metal that can obtain a stable trivalent state, including, but not limited to, iron, manganese, cobalt, chromium, yttrium, and ruthenium. Iron is preferred.

The general reaction process comprehends the production of a mixed-metal chelate of the general formula $CaM(III)EDTA(OH).xH_2O$, wherein M is a trivalent transition metal and x is as defined hereinbefore, by the steps of a) reacting calcium hydroxide or calcium oxide, ethylenediaminetetraacetic acid, and a transition metal-containing material in an aqueous medium, optionally in the presence of an oxidant to convert any transition metal present in a divalent form to its trivalent form; and b) removing water by evaporation.

In a straightforward reaction, a water-soluble salt of the trivalent transition metal is reacted with calcium hydroxide and EDTA according to the following equation:

$$2MX_3 + 5Ca(OH)_2 + 2H_4EDTA \rightarrow 2CaMEDTA(OH) + 3CaX_2 + 8H_2O \quad (1)$$

wherein M is a transition metal, X is an inorganic or organic anion and $H_4EDTA$ is used to distinguish the free acid from the tetraanion. When the calcium salt of $X^-$ is soluble (e.g., $X^-$ is $Cl^-$, $NO_3^-$, $CH_3COO^-$), the bimetallic complex can, in principle, be separated by precipitation or crystallization. When the complex is crystallized from aqueous solution, water may be included in the crystals, either bound directly to one or both of the metals or held in by lattice forces. The amount of water of crystallization will be dependent on solution pH, temperature, and the metals, among other things. Sometimes water can be driven off at high temperature or under vacuum, providing other stoichiometric hydrates or anhydrous materials.

Many transition metals (e.g., Fe, Co, Mn, Ru, etc.) form stable divalent ions as well as trivalent ones. With the addition of an oxidant, the divalent salts of these metals can also be reacted with calcium hydroxide and EDTA to give the same type of bimetallic product:

$$MX_2+2Ca(OH)_2+H_4EDTA+\tfrac{1}{2}H_2O_2 \rightarrow CaMEDTA(OH)+CaX_2+4H_2O \quad (2)$$

Because of its powerful chelating ability for many transition metal ions, aqueous slurries of EDTA are often able to dissolve metal oxides. For example, partially ammoniated slurries of EDTA are commonly reacted with $Fe_3O_4$ to form ferric EDTA solutions used in the photographic industry. Metal oxides can likewise be used to prepare CaMEDTA (OH) solutions according to the following reactions:

$$MO+Ca(OH)_2+H_4EDTA+\tfrac{1}{2}H_2O_2 \rightarrow CaMEDTA(OH)+3H_2O \quad (3)$$

$$M_2O_3+2Ca(OH)_2+2H_4EDTA \rightarrow 2CaMEDTA(OH)+5H_2O \quad (4)$$

$$M_3O_4+3Ca(OH)_2+3H_4EDTA+\tfrac{1}{2}H_2O_2 \rightarrow 3CaMEDTA(OH)+8H_2O \quad (5)$$

wherein M is a transition metal.

Oxidants other than hydrogen peroxide may be employed. A potential advantage to the metal-oxide route is that there is no concomitant formation of calcium salt by-products.

The elemental transition metal may also be used. EDTA will chelate the metal and oxidize it to the divalent state; another oxidant can complete the oxidation to the trivalent state:

$$M+Ca(OH)_2+H_4EDTA+\tfrac{1}{2}H_2O_2 \rightarrow CaMEDTA(OH)+H_2+2H_2O \quad (6)$$

Inasmuch as calcium oxide is converted to calcium hydroxide in aqueous medium, the oxide may replace the hydroxide as the calcium source. The transition metal may be any one that can obtain a stable trivalent state, including, but not limited to, iron, manganese, cobalt, chromium, yttrium, and ruthenium. The transition metal-containing material may be the elemental metal, a salt, an oxide, or a hydroxide. For example, iron may be introduced as iron metal, ferric chloride, ferric nitrate, ferric acetate, ferric citrate, ferrous sulfate, ferrous perchlorate, ferrous oxide, ferric oxide, ferrosoferric oxide, or ferric hydroxide.

Preferably, the transition metal-containing material will be an oxide or hydroxide. As can be seen from an inspection of Equations 1–5, above, the use of a metal salt requires an excess of calcium hydroxide, relative to the transition metal, in order to bind the anions of the salt, resulting in a calcium salt by-product which must be separated from the desired calcium/transition metal/EDTA compound. Use of the elemental transition metal also obviates the need for excess calcium hydroxide, but results in the generation of flammable hydrogen gas.

The molar ratio of EDTA to transition metal can be from about 0.75 to about 1.25, but preferably from 0.9 to 1.1, and more preferably from 0.99 to 1.01. An excess of EDTA or transition metal will result in unreacted material which must be separated from the desired product. The optimum molar ratio of calcium hydroxide (or oxide) to transition metal is dependent on the transition metal-containing reactant. If said reactant is a salt of a trivalent transition metal, the calcium hydroxide:transition metal ratio can be from about 2.0 to about 3.0, preferably 2.3 to 2.7, and more preferably from 2.45 to 2.55. If said reactant is a salt of a divalent transition metal, the calcium hydroxide:transition metal ratio can be from about 1.0 to about 3.0, preferably 1.5 to 2.5, more preferably 1.9 to 2.1. If said reactant is an elemental metal, oxide or hydroxide, the calcium hydroxide:transition metal ratio can be from about 0.5 to 1.5, preferably from 0.7 to 1.3, more preferably from 0.9 to 1.1. Again, the most preferable ratio results in the least unreacted staring material.

When the transition metal-containing material contains the transition metal in a lower-valent state than trivalent (for example, cobaltous chloride or iron metal), the resulting product can be converted to the desired trivalent complex by contacting the mixture with an oxidizing agent. The oxidizing agent need only be a more powerful oxidant than the trivalent transition metal. A practitioner skilled in the art will be able to determine if an oxidant has the desired oxidizing strength from tables of thermodynamic data. Useful oxidants include, but are not limited to, persulfates (e.g., ammonium persulfate or sodium persulfate); periodates (e.g., potassium periodate); permanganates (e.g., potassium permanganate); hypochlorites (e.g., sodium hypochlorite); hydrogen peroxide; and oxygen. Hydrogen peroxide and oxygen are especially preferred, due both to low cost and to the fact that neither introduces counterions to complicate the reaction mixture.

In some cases, the desired calcium/transition metal/EDTA compound will have low solubility in water. In such cases, it is only necessary to filter the reaction mixture to obtain the product. If the product is more soluble in water, it can still be removed by crystallization, either by evaporating the water or by adding a co-solvent in which the product is less soluble. In cases where there are no other calcium salts present (i.e., the transition metal-containing reactant was the element or an oxide or hydroxide), the product can be obtained by spray-drying or otherwise removing all the water.

The amount of water of crystallization in the calcium/transition metal/EDTA compound will vary depending on the transition metal, the pH, and the nuclearity of the complex. The water of crystallization can be removed to a desired degree by heating the compound and/or placing it under a vacuum. Such processes are well-known in the art.

The mixed-metal chelates of the present invention are useful as catalyst precursors and dietary supplements.

The invention will be further clarified by a consideration of the following examples, which are intended to be exemplary of the present invention and should not be construed to limit its scope in any way.

EXAMPLE 1

A two-liter beaker was charged with ethylenediaminetetraacetic acid ($H_4EDTA$, 146 g, 0.500 mole); $Ca(OH)_2$(92.6 g, 1.25 mole); and water (1400 g). The resulting mixture was stirred vigorously; and a solution of $Fe(NO_3)_3$(11.1%Fe by weight) was added quickly (251.5 g, 0.500 mole Fe) to the slurry, immediately giving a dark red solution. The solution was stirred for ten minutes at 45° C. and filtered through a 1.2$\mu$ nylon filter. The filtrate was allowed to evaporate at 70° C. for three days, after which large, red crystals of $CaFeEDTA(OH)\cdot 6.5H_2O$ were removed (82.1 g, 0.158 mole, 31.7% yield). The composition was determined by elemental analysis. Calc. (Found) for $CaFeEDTA(OH)\cdot 6.5H_2O$: C 23.18%(23.01%); H 5.06%(5.27%); N 5.41% (5.41%); Fe 10.78%(10.58%); Ca 7.73%(7.71%).

EXAMPLE 2

A one-liter beaker was charged with $H_4EDTA$ (73 g, 0.25 mole); $Ca(OH)_2$(46.3 g, 0.625 mole); and water (700 g). The mixture was stirred vigorously; and to it was added at once a solution of $FeCl_3 \cdot 6H_2O$ (67.6 g, 0.250 mole) in water (120 g). The resulting brown slurry was heated to 90° C., producing a dark, red-brown solution. Trace insolubles were filtered out, and the filtrate was allowed to evaporate at 65° C. overnight. The product was removed from the mixture by filtration as small, red crystals (12.1 g, 0.023 mole, 9.3%).

EXAMPLE 3

A two-liter, five-necked, round-bottomed flask fitted with a pH probe, a thermometer, and a mechanical stirrer was charged with $H_4EDTA$ (379 g., 1.30 mole); $Ca(OH)_2$ (48.2 g, 0.650 mole); commercial $Fe_3O_4$ (69% Fe by weight, 100 g, 1.24 mole Fe); and water (1200 g). The slurry was stirred vigorously and heated to 93° C. over one hour, during which time the slurry changed color from black to green. The mixture was cooled to 56° C. over fifty minutes; and $Ca(OH)_2$ was added to bring the pH up to 5.4 (24 g, 0.324 mole). During the addition, the green slurry became a deep red solution and then a red slurry. The slurry was sparged with air for three hours, and then more $Ca(OH)_2$ was added to bring the pH up to 5.9 (17.7 g, 0.239 mole). The crimson, crystalline product was removed by filtration and air-dried to give 508 g (0.980 mole, 80.8% yield (based on Ca)). The microcrystalline product was shown to be the same as the product in Example 1 by elemental analysis. Found: C 23.03%; H 5.28%; N 5.46%; Fe 10.68%; Ca 7.69%.

EXAMPLE 4

A 500-ml, three-neck flask, fitted with an overhead mechanical stirrer and thermometer was charged with $H_4EDTA$ (58.5 g, 0.200 mole); $Ca(OH)_2$ (14.8 g, 0.200 mole); and water (350 ml). Vigorous stirring was begun; and Fe powder (11.2 g, 0.200 mole) was added. The resulting mixture was heated to 80° C. to initiate reaction, and then stirred, open to the atmosphere, for four days. The resulting dark red solution displayed a small amount of residual ferrous ion, so 30% aqueous $H_2O_2$ was added (0.1 g, 1 mmole). Filtration of the mixture gave $CaFeEDTA(OH)$ .$6.5H_2O$ as fine, red-orange crystals (31.5 g). Evaporation of the filtrate at 65° C. for one day resulted in the precipitation of another 17.5 g as large, red crystals. Total yield 49 g (0.0945 mole, 47%).

EXAMPLE 5

A 2.0046-gram sample of the product from Example 3 (3.868 millimoles) was placed in a Petri dish and set in an oven at 115° C. for three days. The resulting tan powder was shown to be $CaFeEDTA(OH)$ by elemental analysis. Calc. (Found): C 29.94% (29.90%); H 3.27% (3.32%); N 6.98% (7.01%); Fe 13.92% (14.19%); Ca 9.99% (10.02%). The yield was 1.5307 g (3.816 mmoles).

EXAMPLE 6

A one-liter beaker was charged with $H_4EDTA$ (73.1 g, 0.250 mole); $Ca(OH)_2$ (37.0 g, 0.500 mole); and water (400 g). The mixture was stirred rapidly, and to the resulting slurry was added a solution of $Co(NO_3)_2$. $6H_2O$ (72.7 g, 0.250 mole) in water (300 g). The resulting mixture was warmed gently to give a purple solution. To this was added dropwise 30% aqueous $H_2O_2$ (14.2 g, 0.125 mole), causing a mild exotherm and darkening of the solution. The solution was stirred for one hour and then filtered to remove a small amount of brown, insoluble material. The solution was allowed to evaporate at 65° C. for four days, after which purple crystals of $CaCoEDTA(OH).5.5H_2O$. (36.5 g, 0.072 mole). The composition was determined by elemental analysis. Calc. (Found) for $CaCoEDTA(OH).5.5H_2O$: C 23.86% (24.53%); H 4.81% (5.00%); N 5.57% (5.86%); Ca 7.96% (8.63%); Co 11.71% (11.62%).

EXAMPLE 7

A 1.0982-g sample of $CaCoEDTA(OH).5.5H_2O$ (2.182 mmoles) was placed in a Petri dish and heated at 105° C. for three hours, giving 0.8299 g of $CaCoEDTA(OH)$ (2.053 mmoles) as a pink powder.

EXAMPLE 8

A one-liter beaker was charged with $H_4EDTA$ (73.1 g, 0.250 mole); $Ca(OH)_2$ (46.3 g, 0.625 mole); and water (450 g). The mixture was stirred rapidly, and to the resulting slurry was added a solution of $CrCl_3$. $6H_2O$ (66.6 g, 0.250 mole) in water (250 g). The initially green mixture quickly became a blue-violet slurry, which was stirred another half-hour. The product, $CaCrEDTA(OH).7H_2O$, was removed by filtration, washed with water (500 g), and air-dried at 40° C., giving 92.9 g. Elemental analyses show that the product contained a by-product wherein some of the calcium had been replaced with chromium. Calc. for $CaCrEDTA(OH).7H_2O$: C 22.95%; H 5.20%, N 5.35%; Ca 7.66%; Cr 9.93%. Calc. for $Ca_{0.85}Cr_{1.15}EDTA(OH).7H_2O$: C 22.87%; H 5.18%; N 5.33%; Ca 6.49%, Cr 11.39%. Found: C 22.50%; H 5.34%; N 5.23%; Ca 6.55%; Cr 11.63%.

What is claimed is:

1. A mixed-metal chelate having the following general formula $CaM(III)EDTA(OH).xH_2O$ wherein M is a trivalent transition metal and x is 0, 0.5, 1, 1.5, 2, 2.5, 3, 3.5, 4, 4.5, 5, 5.5, 6, 6.5, 7, 7.5, or 8.

2. The mixed-metal chelate according to claim 1 wherein M in the formula is trivalent iron.

3. The mixed-metal chelate according to claim 1 wherein M in the formula is trivalent cobalt.

4. The mixed metal-chelate according to claim 1 wherein M in the formula is trivalent chromium.

5. The mixed metal-chelate according to any one of claims 1 to 4 wherein x in the formula is 0.

6. The mixed-metal chelate according to any one of claims 1 to 4 wherein x in the formula is 5.5.

7. The mixed-metal chelate according to any one of claims 1 to 4 wherein x in the formula is 6.5.

8. The mixed-metal chelate according to any one of claims 1 to 4 wherein x in the formula is 7.

9. A process for preparing mixed-metal chelates of the general formula $CaM(III)EDTA(OH).xH_2O$, wherein M is a trivalent transition metal and x is 0, 0.5, 1, 1.5, 2, 2.5, 3, 3.5, 4, 4.5, 5, 5.5, 6, 6.5, 7, 7.5, or 8, said process comprising the steps of a) reacting calcium hydroxide or calcium oxide, ethylenediaminetetraacetic acid, and a transition metal-containing material in an aqueous medium; and b) separating the formed mixed-metal chelate by filtration or evaporation.

10. The process according to claim 9 wherein the reaction in step a) is conducted in the presence of an oxidant to convert any transition metal present in a divalent form to its trivalent form.

11. The process according to claim 9 or claim 10 wherein the transition metal-containing material is an elemental transition metal, a transition metal salt, or a transition metal oxide.

12. The process according to claim 9 or claim 10 wherein the molar ratio of EDTA to transition metal is from about 0.75 to 1.1.

13. The process according to 11 wherein the transition metal-containing material is elemental iron, a ferric salt or an iron oxide.

14. The process according to 13 wherein the transition metal-containing material is ferric chloride or ferric nitrate.

15. The process according to claim 13 wherein the iron oxide is ferrosoferric oxide.

16. The process according to claim 10 wherein the reaction in step a) is conducted in the presence of air or hydrogen peroxide as the oxidant.

17. The process according to claims 13 or 15 wherein the reaction in step a) is conducted in the presence of air or hydrogen peroxide as the oxidant.

18. The process according to claim 11 wherein the transition metal-containing material is elemental cobalt, a cobalt salt or a cobalt oxide.

19. The process according to claim 18 wherein the cobalt salt is cobaltous nitrate.

20. The process according to claim 18 or claim 19 wherein the reaction in step a) is conducted in the presence of an oxidant.

21. The process according to claim 20 wherein the oxidant is air or hydrogen peroxide.

22. The process according to 11 wherein the transition metal-containing material is elemental chromium, a chromium salt or a chromium oxide.

23. The process according to claim 22 wherein the transition metal-containing material is a chromium salt.

24. The process according to claim 23 wherein the chromium salt is chromic chloride.

* * * * *